United States Patent [19]

Bersier et al.

[11] 4,311,565

[45] Jan. 19, 1982

[54] ELECTROCHEMICAL PROCESS FOR THE PRODUCTION OF BENZANTHRONE

[75] Inventors: Jacques Bersier, Riehen; Horst Jäger, Bettingen; Hansrudolf Schwander, Riehen, all of Switzerland

[73] Assignee: Ciba-Geigy AG, Basel, Switzerland

[21] Appl. No.: 151,482

[22] Filed: May 19, 1980

[30] Foreign Application Priority Data

May 30, 1979 [CH] Switzerland ............... 5034/79

[51] Int. Cl.$^3$ .................. C07C 50/22; C25B 3/04
[52] U.S. Cl. .................. 204/73 R; 204/59 R; 204/72; 204/75; 260/352; 260/364
[58] Field of Search ............ 204/59 R, 72 R, 73 R, 204/76, 75, 77; 260/352, 364

[56] References Cited

U.S. PATENT DOCUMENTS

| | | | |
|---|---|---|---|
| 798,104 | 8/1905 | Isler | 260/352 |
| 3,925,172 | 12/1975 | Voorhies | 204/72 |
| 4,102,757 | 7/1978 | Chillier-Duchatel et al. | 204/73 |
| 4,127,595 | 11/1978 | Matsuura et al. | 260/352 |

FOREIGN PATENT DOCUMENTS

| | | | |
|---|---|---|---|
| 447323 | 3/1948 | Canada | 204/77 |
| 271528 | 5/1970 | U.S.S.R. | 204/73 |

*Primary Examiner*—Winston A. Douglas
*Assistant Examiner*—Raymond K. Covington
*Attorney, Agent, or Firm*—Sprung, Felfe, Horn, Lynch & Kramer

[57] ABSTRACT

An electrochemical process for the production of benzanthrone by reaction of anthraquinone as, starting material, with glycerol, which process comprises reducing anthraquinone, which may additionally contain electronegative substituents, at the cathode in an electrolytic cell in acid medium, and simultaneously cyclizing the reduced semiquinone form with glycerol to produce the corresponding benzanthrone. The novel process affords numerous advantages compared with chemical reduction methods.

8 Claims, No Drawings

ELECTROCHEMICAL PROCESS FOR THE PRODUCTION OF BENZANTHRONE

The present invention relates to an electrochemical process for the production of benzanthrone by reaction of anthraquinone, as starting material, with glycerol, which process comprises reducing anthraquinone, which may additionally contain electronegative substituents, e.g. OH or halogen, at the cathode in an electrolytic cell in acid medium, and simultaneously cyclising the reduced semiquinone form with glycerol to produce the corresponding benzanthrone.

It is known to produce corresponding benzanthrones by other methods; but reduction systems have always been required in which mainly metals were employed as reducing agents. For example, the production of benzanthrone from anthraquinone and glycerol was described early on in Bally, Berichte Vol. 38 (1905). Since then, various attempts have been made to improve this conventional method of cyclisation.

For example, the use of aniline as reducing agent (Scholl and Bally, Berichte Vol. 44, 1956 (1911)] has not attained economic importance. The use of e.g. 70 to 90% sulfuric acid as reduction medium, and a metal such as iron, zinc, aluminium or copper, as reducing agent, is described in the following publications: U.S. Pat. No. 1,896,147 (reducing agent Fe); U.S. Pat. No. 2,034,485 and USSR Patent specification No. 401.130 (reducing agent Cu+Fe); A. M. Lahin, Zhur. Obschei Khim. 18, 308 (1948); cf. CA 44, 1079b (reducing agent Zn, Al, CuSO4); U.S. Pat. No. 1,791,309 (reducing agent Zn+Al); Of these reducing agents, iron has aquired the greatest practical importance. However, the use of iron as sole reducing agent has great economic and ecological drawbacks, for at least 2 moles of iron per mole of anthraquinone have to be employed. The consequence is that, per mole of benzanthrone, 2.0 moles of iron sulfate (or, per 1000 g of benzanthrone, 1320 g of iron sulfate) occur as waste product. In addition, substantial amounts of waste sulfuric acid are formed, as the sulfuric acid has to be diluted to about 20% in order to isolate the benzanthrone. This dilute sulfuric acid then either has to be regenerated to concentrated sulfuric acid with great expenditure of energy, or its elimination constitutes an environmental problem.

The reaction in accordance with the novel process takes place in situ in one step. The synthesis proceeds e.g. in accordance with the following reaction scheme:

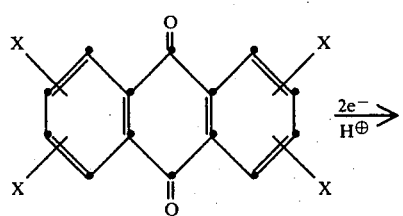

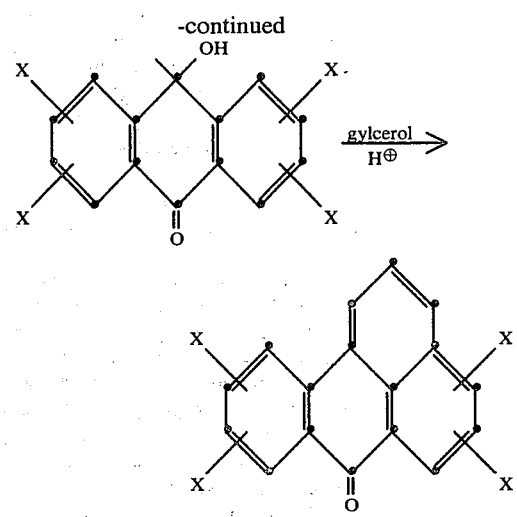

wherein X is OH, O-alkyl of 1 to 4 carbon atoms, halogen, and X is 0 or 1.

The molar ratios of quinoid compound to glycerol can vary within wide limits between 1:1 and 1:10 in the novel process, but the best yields are obtained employing a molar ratio of quinoid compound to glycerol of 1:1.5 to 1:2.5. Reaction media are advantageously strong mineral acids, especially sulfuric acid. This latter can be employed in a concentration of 60–98%, with the preferred concentration range however being from 80–90%. The use of organic inert acids is also possible.

The electrochemical synthesis proceeds at a temperature in the range between 20° and 150° C. However, on account of the solubility or suspendibility of the quinoid compounds e.g. in sulfuric acid electrolytes, it is necessary to choose operating temperatures in the range from about 80° to 120° C. in order to be able to carry out the process in technically interesting concentrations.

It is advantageous to carry out the process in an inert gas atmosphere so that no oxidative reverse reaction takes place. It is sufficient to introduce a weak flow of e.g. nitrogen into the reaction vessel above the surface of the reaction medium.

The electrolytic cell can be any cell with diaphragm. The diaphragm must be resistant to concentrated and dilute mineral acids, e.g. sulfuric acid, hydrochloric acid, hydrofluoric acid, and to organic acids, e.g. acetic acid, formic acid, organic sulfonic acids and other acids. Examples of suitable diaphragms are glass or polymer compounds such as Nafion ®. The acid solutions of reaction substrate and product can also contain organic solvents. In addition, it is also possible that the electrolyte containing acid and optionally organic solvent does not have a dehydrating action and that the synthesis proceeds only via electrochemically produced intermediates which can also enter into other reactions.

As electrolytic cells it is also possible to use monocells, i.e. which require no diaphragm.

Suitable cathodes and anodes are materials conventionally employed for electroorganic reactions, such as metals, metal alloys, activated metals, metallic oxide electrodes, carbon electrodes, "Glassy Carbon ®  electrodes".

The reaction product can be isolated in conventional manner. The sulfuric acid is diluted e.g. to a concentration of about 60% and the precipitated product is collected by filtration and washed neutral, or the product is extracted from the 60% sulfuric acid with a commercially available solvent.

Suitable solvents for isolating the reaction product by extraction and phase separation are higher boiling, inert organic solvents, in particular halogenated hydrocarbons, most preferably chlorobenzenes, for example monochlorobenzene.

The extraction temperature (for taking up the product in the organic solvent) is 70° to 110° C., advantageously 90° to 100° C.

In addition to the advantages already referred to, an important advantage of the novel process of the present invention is that both the inert organic solvent optionally employed and the 60% sulfuric acid can be recycled virtually in their entirety. Other by-products or environmentally harmful waste products do not result. In addition, the product is obtained in such purity that further customary purifying operations can be dispensed with. Accordingly, the process of the invention affords exceptional ecological and economic advantages. The reaction products are important intermediates for the production of dyes and pigments, e.g. as described by J. Houben and W. Fischer, "Anthracen and die Anthrachinone", Vol. II, pp. 774–777 (1929), or by Venkataraman in "Synthetic Dyes", Vol. II, pp. 963–965 (1952).

The following Examples describe the process of the invention in more detail.

EXAMPLE 1

10.0 g (0.048 mole) of anthraquinone are suspended in 110 ml of 85% sulfuric acid in an electrolytic cell made of glass and consisting of a cathode space (Hg cathode) and anode space (Pt anode) separated by a glass diaphragm, the potential being measured against a Hg/HgSO$_4$ reference electrode, and the solution is heated to 100° C. In an inert gas atmosphere of N$_2$, the anthraquinone is reduced to oxanthrone at the cathode after applying current, while simultaneously adding 9.8 g (0.1 mole) of glycerol dropwise. After the passage of 10700 coulomb per 0.048 mole of anthraquinone the electrolysis is discontinued, the 85% sulfuric acid is diluted to a concentration of 60%, and the precipitated benzanthrone is filtered and washed neutral. The crude benzanthrone is dried. It is obtained in such purity that it can be used immediately in further reactions, e.g. for producing violanthrone or 3-bromobenzanthrone.

Yield: 9.2 g ($\triangleq$ 83.25% of theory) of benzanthrone with a melting point of 167°–169° C.

EXAMPLE 2

A second experiment was carried out repeating the procedure of Example 1, except that the temperature was 90° C. and the flow of current 11850 coulomb.

Yield: 10.8 g ($\triangleq$ 97.74% of theory) of benzanthrone with a melting point of 165°–168° C.

EXAMPLE 3

15.0 (0.072 mole) of anthraquinone are suspended between a Hg cathode and a Pt anode in 250 ml of 85% sulfuric acid in an electrolytic cell made of glass which contains no diaphragm (monocell), the potential being measured against a Hg/HgSO$_4$ reference electrode, and the solution is heated to 100° C. In an inert gas atmosphere of N$_2$ the anthraquinone is reduced at the cathode to oxanthrone after applying current, while simultaneously adding 11.9 g (0.13 mole) of glycerol dropwise. After the passage of 17000 coulomb, the elctrolysis is discontinued, the 85% sulfuric acid is diluted to a concentration of 60%, and the precipitated benzanthrone is filtered with suction and washed neutral. The crude benzanthrone is dried.

Yield: 12. 4 g ($\triangleq$ 74.9% of theory) of benzanthrone with a melting point of 158°–162° C.

EXAMPLE 4

As described in Example 1, hydroxy-substituted benzanthrones are prepared in the same electrolytic cell from 1-methoxyanthraquinone (4a), 1,2-dihydroxyanthraquinone (4b) and 2-hydroxyanthraquinone (4c). The results are reported in the table.

| compound mole | glycerol | H$_2$SO$_4$ | coulomb | temperature | yield | products |
|---|---|---|---|---|---|---|
| 4a 0.05 | 0.1 mole | 150 ml 96% | 28000 | 90° C. | 70% | 6-hydroxybenzanthrone 16.0% 6-methoxybenzanthrone 79.3% |
| 4b 0.025 | 0.05 mole | 200 ml 85% | 7200 | 95° C. | 30% | 5,6-dihydroxybenzanthrone and 70% of 1,2-dihydroxyanthraquinone recovered |
| 4c 0.025 | 0.05 mole | 150 ml 85% | 8800 | 95° C. | 66% | 4-hydroxybenzanthrone |

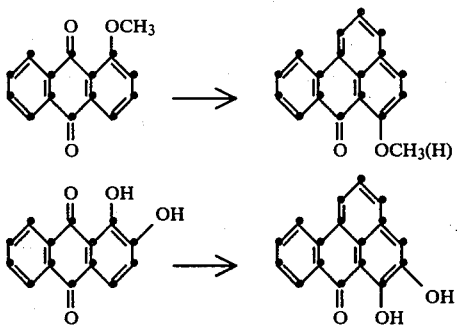

-continued

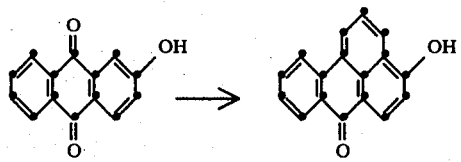
4c

EXAMPLE 5

As described in Example 1, substituted benzanthrone is produced in the same electrolytic cell from 1-chloroanthraquinone. The results are reported in the table below.

| compound mole | glycerol | $H_2SO_4$ | coulomb | temperature | yield | products |
|---|---|---|---|---|---|---|
| 5a 0.15 mole | 0.5 mole | 500 ml 85% | 60000 | 85° C. | 29.5% | 6-chlorobenzanthrone 86.1% 6-hydroxybenzanthrone 13.6% |

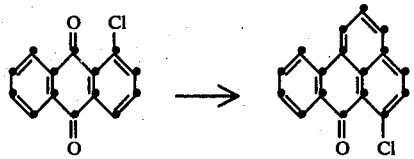
5a

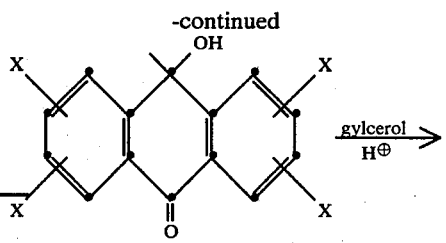

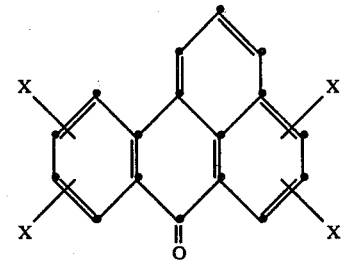

wherein X is OH, O-alkyl of 1 to 4 carbon atoms, halogen, and X is 0 or 1.

3. A reaction according to claim 1 which is carried out at a temperature between 20° and 150° C.

4. A reaction according to claim 1 which is carried out at a temperature between 80° and 120° C.

5. A reaction according to claim 1, wherein a mineral acid is used as acid medium.

6. A reaction according to claim 1, wherein sulfuric acid having a concentration of 60 to 98% is used as acid medium.

7. A reaction according to claim 1, wherein the molar ratio of anthraquinone compound to glycerol is 1:1 to 1:10.

8. A reaction according to claim 1 which comprises reducing anthraquinone at the cathode in 85% sulfuric acid in an electrolytic cell to oxanthrone and simultaneously adding glycerol in the molar ratio 1:2, diluting the acid to a concentration pf 60% after completion of the reaction, and washing the benzanthrone obtained as product neutral and washing it.

What is claimed is:

1. An electrochemical process for the production of benzanthrone by reaction of anthraquinone, as starting material, with glycerol, which process comprises reducing anthraquinone, which may additionally contain electronegative substituents, to oxanthrone at the cathode in an electrolytic cell in acid medium, and simultaneously cyclising the reduced semiquinone form with glycerol to produce the corresponding benzanthrone.

2. A cyclisation reaction according to claim 1 in accordance with the reaction scheme

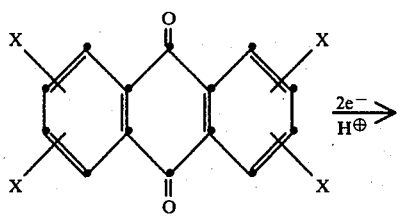

* * * * *